(12) United States Patent
Yin et al.

(10) Patent No.: US 11,016,029 B2
(45) Date of Patent: May 25, 2021

(54) MEASURING CHAMBER, WORKING METHOD OF MEASURING CHAMBER, CHEMILUMINESCENCE MEASUREMENT METHOD OF MEASURING CHAMBER AND CHEMILUMINESCENCE DETECTOR

(71) Applicant: Shenzhen New Industries Biomedical Engineering Co., Ltd., Guangdong (CN)

(72) Inventors: Li Yin, Guangdong (CN); Liang Zhu, Guangdong (CN); Yi Hu, Guangdong (CN); Dingping Ban, Guangdong (CN); Junhui Tang, Guangdong (CN); Jinhong Wu, Guangdong (CN)

(73) Assignee: Shenzhen New Industries Biomedical Engineering Co., Ltd., Guangdong (CN)

( * ) Notice: Subject to any disclaimer, the term of this patent is extended or adjusted under 35 U.S.C. 154(b) by 373 days.

(21) Appl. No.: 16/137,550

(22) Filed: Sep. 21, 2018

(65) Prior Publication Data

US 2019/0094145 A1    Mar. 28, 2019

(30) Foreign Application Priority Data

Sep. 28, 2017    (CN) .......................... 201710900630.8

(51) Int. Cl.
*G01N 21/76*    (2006.01)
*G01N 35/02*    (2006.01)
(Continued)

(52) U.S. Cl.
CPC ........... *G01N 21/76* (2013.01); *G01N 35/025* (2013.01); *G01N 35/026* (2013.01);
(Continued)

(58) Field of Classification Search
CPC .... G01N 21/76; G01N 35/025; G01N 35/026; G01N 35/04; G01N 35/00; G01N 33/543;
(Continued)

(56) References Cited

U.S. PATENT DOCUMENTS 5,837,195 A * 11/1998 Malek .................... G01N 21/13
422/52
2006/0013729 A1* 1/2006 Carey ................... B01F 9/0025
422/63

FOREIGN PATENT DOCUMENTS

CN          1793383 A      6/2006
CN        101980006 A      2/2011
(Continued)

*Primary Examiner* — Kathryn Wright
*Assistant Examiner* — Curtis A Thompson
(74) *Attorney, Agent, or Firm* — Yu Gang

(57) ABSTRACT

The present disclosure relates to a measuring chamber, a working method of the measuring chamber, a chemiluminescence measurement method of the measuring chamber and a chemiluminescence detector. The measuring chamber includes a dark chamber, a first substrate nozzle, a photomultiplier detection component, a waste liquor adsorption needle component, a reaction cup turntable and a plurality of reaction cup processing stations; the reaction cup turntable is provided in the measuring chamber rotationally; and the plurality of reaction cup processing stations are sealed in a mutually light-isolated manner. When the instrument works, reaction cups in the reaction cup turntable are moved in the dark chamber; and after the reaction cups are moved to corresponding processing stations for processing the reaction cups, the plurality of different processing stations for processing, the reaction cups may simultaneously process the reaction cups moved to the corresponding reaction cup processing stations.

19 Claims, 6 Drawing Sheets

(51) Int. Cl.
  *G01N 35/00* (2006.01)
  *G01N 35/04* (2006.01)
  *G01N 17/00* (2006.01)
  *G01N 27/64* (2006.01)
  *G01N 21/13* (2006.01)
  *G01N 21/64* (2006.01)
  *G01N 33/543* (2006.01)
  *G01N 21/75* (2006.01)

(52) U.S. Cl.
  CPC ........... *G01N 17/002* (2013.01); *G01N 21/13* (2013.01); *G01N 21/64* (2013.01); *G01N 21/6428* (2013.01); *G01N 21/6452* (2013.01); *G01N 27/64* (2013.01); *G01N 33/543* (2013.01); *G01N 35/00* (2013.01); *G01N 35/02* (2013.01); *G01N 35/04* (2013.01); *G01N 2021/752* (2013.01); *G01N 2035/00306* (2013.01); *G01N 2035/0444* (2013.01); *G01N 2223/64* (2013.01)

(58) Field of Classification Search
  CPC ............... G01N 21/64; G01N 21/6452; G01N 21/6428; G01N 21/13; G01N 35/02; G01N 2223/64; G01N 27/64; G01N 17/002; G01N 2035/00306; G01N 2035/0444; G01N 2021/752; G01N 21/01
  See application file for complete search history.

(56) References Cited

FOREIGN PATENT DOCUMENTS

| | | |
|---|---|---|
| CN | 203519500 U | 4/2014 |
| CN | 205991944 U | 3/2017 |
| CN | 107132215 A | 9/2017 |
| CN | 206876584 U | 1/2018 |
| JP | H0467035 A | 3/1992 |
| JP | H0953982 A | 2/1997 |
| JP | 2015022004 A | 2/2015 |
| KR | 20100025336 A | 3/2010 |

\* cited by examiner

MEASURING CHAMBER, WORKING METHOD OF MEASURING CHAMBER, CHEMILUMINESCENCE MEASUREMENT METHOD OF MEASURING CHAMBER AND CHEMILUMINESCENCE DETECTOR

TECHNICAL FIELD

The present disclosure relates to a technical field of medical appliances, and more particularly, to a chemiluminescence detector.

BACKGROUND

A bio-chemiluminescence immunoassay is a non-radioactive label immunoassay method established based on theoretical basis of a radioimmunodetection technology and with a luminescent marker as a tracking signal. It has the advantages of high sensitivity, wide limit range, easy operation and easy automation implementation, etc. At present, along with the high-speed development of a biomedical device, certain conditions for implementing complete automation of a bio-chemiluminescence detector have been achieved and the bio-chemiluminescence detector based on the bio-chemiluminescence immunoassay has gradually become a mainstream medical diagnostic device.

A measuring chamber is a key unit affecting the accuracy of a measurement result as well as a measurement speed of the chemiluminescence detector, and particularly, the air-tightness of the measuring chamber determines the accuracy of the measurement result and the measurement speed. For example, a measuring chamber disclosed by a Chinese patent application no. CN205449807U can only work serially, that is, only one reaction cup can be placed into the measuring chamber and a flip cover is closed for measurement at one time. After the measurement is finished, the flip cover is opened a gain to take out the reaction cup. When one reaction cup processing station of the measuring chamber works, other reaction cup processing stations are in an idle state, and thus operations such as reaction cup in-out, excitation substrate pumping, photon measurement and waste liquor disposal cannot be processed in parallel, and the measurement speed of the instrument is seriously reduced.

SUMMARY

In view of this, for the above technical problems, it is necessary to provide a measuring chamber capable of improving the measurement speed and the measurement accuracy, a working method of the measuring chamber, a chemiluminescence measurement method of the measuring chamber and a chemiluminescence detector.

The present disclosure provides a measuring chamber for processing multiple reaction cup processing stations in parallel, which includes a dark chamber, a first substrate nozzle, a photomultiplier detection component, a waste liquor adsorption needle component, a reaction cup turntable and a plurality of reaction cup processing stations; the reaction cup turntable is provided in the measuring chamber rotationally; and the plurality of reaction cup processing stations are sealed in a mutually light-isolated manner.

The present disclosure provides a measuring chamber for processing multiple reaction cup processing stations in parallel, which includes a first reaction cup processing station, a reaction cup being placed into or taken out of the measuring chamber at the first reaction cup processing station; a second reaction cup processing station, a first substrate nozzle being provided at the second reaction cup processing station so as to add an excitation substrate I to the reaction cup respectively; a third reaction cup processing station, a photomultiplier detection component being provided at the third reaction cup processing station; and a fourth reaction cup processing station, a waste liquor adsorption needle component being provided at the fourth reaction cup processing station so as to extract waste liquor in the reaction cup; and the third reaction cup processing station and the adjacent second reaction cup processing station and the fourth reaction cup processing station are sealed in a mutually light-isolated manner.

The present disclosure provides a measuring chamber for processing multiple reaction cup processing stations in parallel, which includes a bottom plate, an outer shell, an upper cover, a first substrate, nozzle, a photomultiplier detection component, a waste liquor adsorption needle component and a reaction cup turntable; the bottom plate, the outer shell and the upper cover are enclosed into a holding space; the reaction cup turntable is rotationally arranged in the holding space; a plurality of light-isolated components are provided between the reaction cup turntable and the upper cover; and the plurality of light-isolated components can be rotated with the reaction cup turntable together relative to the upper cover, so as to divide the reaction cup turntable into a plurality of reaction cup holding areas sealed in a mutually light-isolated manner.

The present disclosure provides a working method of the measuring chamber, which includes the following steps:

1) a first reaction cup loaded with a to-be-tested sample is placed into a first reaction cup holding cavity of a reaction cup turntable at a first, reaction cup processing station;

2) the reaction cup turntable is rotated so as to move the first reaction cup holding cavity to a second reaction cup processing station and move a second reaction cup holding cavity of the reaction cup, turntable to the first reaction cup processing station, and then the following steps are executed synchronously:

(1) a first substrate nozzle adds an excitation substrate I to the first reaction cup at the second reaction cup processing station; and (2) a second reaction cup is placed into the second reaction cup holding cavity at the first reaction cup processing station;

3) the reaction cup turntable is rotated so as to move the first reaction cup holding cavity to a third reaction cup processing station, move the second reaction cup holding cavity to the second reaction cup processing station, and move a third reaction cup holding cavity of the reaction cup turntable to the first reaction cup processing station, and then the following steps are executed synchronously:

(1) a second substrate nozzle adds an excitation substrate II to the first reaction cup, and a photomultiplier detection component measures the number of photons of the first reaction cup;

(2) the first substrate nozzle adds the excitation substrate I to the second reaction cup; and (3) a third reaction cup is placed into the third reaction cup holding cavity at the first reaction cup processing station;

4) the reaction cup turntable is rotated so as to move the first reaction cup holding cavity to a fourth reaction cup processing station, move the second reaction cup holding cavity to the third reaction cup processing station, move the third reaction cup holding cavity to the second reaction cup processing station and move a fourth reaction cup of the reaction cup turntable to the first reaction cup processing station, and then the following steps are executed synchronously:
(1) the waste liquor adsorption needle component extracts away waste liquor in the first reaction cup;
(2) the second substrate nozzle adds the excitation substrate II to the second reaction cup, and a photomultiplier detection component measures the number of photons of the second reaction cup;
(3) the first substrate nozzle adds the excitation substrate I to the third reaction cup; and
(4) a fourth reaction cup is placed into the fourth reaction cup holding cavity at the first reaction cup processing station; and
5) the reaction cup turntable is rotated so as to move the first reaction cup holding cavity to the first reaction cup processing station, move the second reaction cup holding cavity to the fourth reaction cup processing station, move the third reaction cup holding cavity to the third reaction cup processing station and move the fourth reaction cup holding cavity to the second reaction cup processing station, and then the following steps are executed synchronously:
(1) the first reaction cup is taken out and a fifth reaction cup is placed into at the first reaction cup processing station;
(2) the waste liquor adsorption needle component extracts away waste liquor in the second reaction cup;
(3) the second substrate nozzle adds the excitation substrate II to the third reaction cup, and the photomultiplier detection component measures the number of photons of the third reaction cup; and
(4) the first substrate nozzle adds the excitation substrate I to the fourth reaction cup.

The present disclosure provides a chemiluminescence measurement method of the measuring chamber, which includes the following steps: a first reaction cup loaded with a to-be-tested sample is placed into a first reaction cup holding cavity of a reaction cup turntable at a first reaction cup processing station; the reaction cup turntable is rotated so as to move the first reaction cup holding cavity to a second reaction cup processing station, and a first substrate nozzle adds an excitation substrate I to the first reaction cup at the second reaction cup processing station; the reaction cup turntable is rotated so as to move the first reaction cup holding cavity to a third reaction cup processing station, a second substrate nozzle adds an excitation substrate II to the first reaction up and a photomultiplier detection component measures the number of photons of the first reaction cup; the reaction cup turntable is rotated so as to move the first reaction cup holding cavity to a fourth reaction cup processing station, and a waste liquor adsorption needle component extracts away waste liquor of the first reaction cup; and the reaction cup turntable is rotated so as to move the first reaction cup holding cavity to the first reaction cup processing station, and the first reaction cup is taken out and a new reaction cup is placed into at the first reaction cup processing station.

The present disclosure provides a chemiluminescence detector, which includes a measuring chamber; the measuring chamber includes a dark chamber, a first substrate nozzle, a photomultiplier detection component, a waste liquor adsorption needle component, a reaction cup turntable and a plurality of reaction cup processing stations; the reaction cup turntable is provided in the measuring chamber rotationally; and the plurality of reaction cup processing stations are sealed in a mutually light-isolated manner.

The present disclosure provides a chemiluminescence detector, which includes a measuring chamber; the measuring chamber includes a first reaction cup processing station, a reaction cup being placed into or taken out of the measuring chamber at the first reaction cup processing station; a second reaction cup processing station, a first substrate nozzle being provided at the second reaction cup processing station so as to add an excitation substrate I to the reaction cup respectively; a third reaction cup processing station, a photomultiplier detection component being provided at the third reaction cup processing station; and a fourth reaction cup processing station, a waste liquor adsorption needle component being provided at the fourth reaction cup processing station so as to extract waste liquor in the reaction cup; and the third reaction cup processing station and the adjacent second reaction cup processing station and the fourth reaction cup processing station are sealed in a mutually light-isolated manner.

The present disclosure provides a chemiluminescence detector, which includes a measuring chamber; the measuring chamber includes a bottom plate, an outer shell, an upper cover, a first substrate nozzle, a photomultiplier detection component, a waste liquor adsorption needle component and a reaction cup turntable; the bottom plate, the outer shell and the upper cover are enclosed into a holding space; the reaction cup turntable is rotationally arranged in the holding space; a plurality of light-isolated components are provided between the reaction cup turntable and the upper cover; and the plurality of light-isolated components can be rotated with the reaction cup turntable together relative to the upper cover, so as to divide the reaction cup turntable into a plurality of reaction cup holding areas sealed in a mutually light-isolated manner.

The present disclosure provides a working method of the measuring chamber, which includes the following steps executed synchronously:
S1: a first reaction cup loaded with a to-be-tested sample is placed into the measuring chamber at a reaction cup entering station; and
S2: a photomultiplier detection component measures the number of photons of the second reaction cup at a reaction cup measuring station.

According to the measuring chamber, the working method of the measuring chamber, the chemiluminescence measurement method of the measuring chamber and the chemiluminescence detector, when a driving mechanism drives the reaction cup turntable to rotate in the dark chamber, the reaction cups in the a plurality of reaction cup holding cavities are simultaneously moved in the dark chamber with the reaction cup turntable; and after the reaction cups are conveyed to corresponding processing stations for processing the reaction cups, the plurality of different processing stations for processing the reaction cups can simultaneously perform parallel processing on the reaction cups conveyed to the corresponding reaction cup processing stations, so that the measuring chamber implements simultaneous work of reaction cup in-out, excitation substrate adding, photon measurement and waste liquor disposal at the different reaction cup processing stations, and thus the measurement speed of the instrument is greatly improved.

In some embodiments, the third reaction cup processing station (measurement reaction cup processing station) and the adjacent reaction cup processing stations are sealed in a light-isolated manner; and the reaction cup at the third reaction cup processing station (measurement reaction cup processing station) is not interfered by light rays generated by the reaction cup at other reaction cup processing stations during measurement.

In some embodiments, through the plurality of light-isolated components, the reaction cup turntable of the measuring chamber is divided into a plurality of individual areas, and the light isolation effects among the plurality of individual areas is relatively good, so that in a process when the plurality of reaction cup processing stations of the measuring chamber work in parallel, the plurality of reaction cups working at each of the reaction cup processing stations in parallel do not produce light interference mutually.

In some embodiments, a zigzag labyrinth structure also has dynamic sealing effect, so that, the interference of the outside light rays to the measurement accuracy can be eliminated and the problem of residual luminous interference due to the fact that multiple reaction cups in a same measuring chamber are processed simultaneously in parallel is also solved.

BRIEF DESCRIPTION OF THE DRAWINGS

In order to describe the technical solutions in the embodiments of the present disclosure or in the conventional art more clearly, a simple introduction on the accompanying drawings which are needed in the description of the embodiments or the conventional art is given below. Apparently, the accompanying drawings in the description below are merely some of the embodiments of the present disclosure, based on which other drawings may be obtained by those of ordinary skill in the art without any creative effort.

DETAILED DESCRIPTION OF THE EMBODIMENTS

In order to understand the present disclosure conveniently, the measuring chamber, the parallel working method for the multiple reaction cup processing stations of the measuring chamber, the chemiluminescence measurement method and the chemiluminescence detector will be described more comprehensively with reference to relevant accompanying drawings. In the accompanying drawings, some embodiments of the measuring chamber, the parallel working method for the multiple reaction cup processing stations of the measuring chamber, the chemiluminescence measurement method and the chemiluminescence detector are given. However, the measuring chamber, the parallel working method for the multiple reaction cup processing stations, of the measuring chamber, the chemiluminescence measurement method and the chemiluminescence detector may be implemented in many different forms, and are not limited to the embodiments described herein. On the contrary, the purposes of providing these embodiments are to enable contents disclosed in the measuring chamber, the parallel working method for the multiple reaction cup processing stations of the measuring chamber, the chemiluminescence measurement method and the chemiluminescence detector to be more thorough and comprehensive.

Unless otherwise specified, all technical and scientific terms used herein have the same meaning generally understood by a person skilled in the art of the present disclosure. As used herein, terms used by the measuring chamber, the parallel working method for the multiple reaction cup processing stations of the measuring chamber, the chemiluminescence measurement method and the chemiluminescence detector in the description are merely for describing the specific embodiments but not to limit the present disclosure. As used herein, terms "and/or" include any and all combinations of one or more relevant items.

Figure 1:
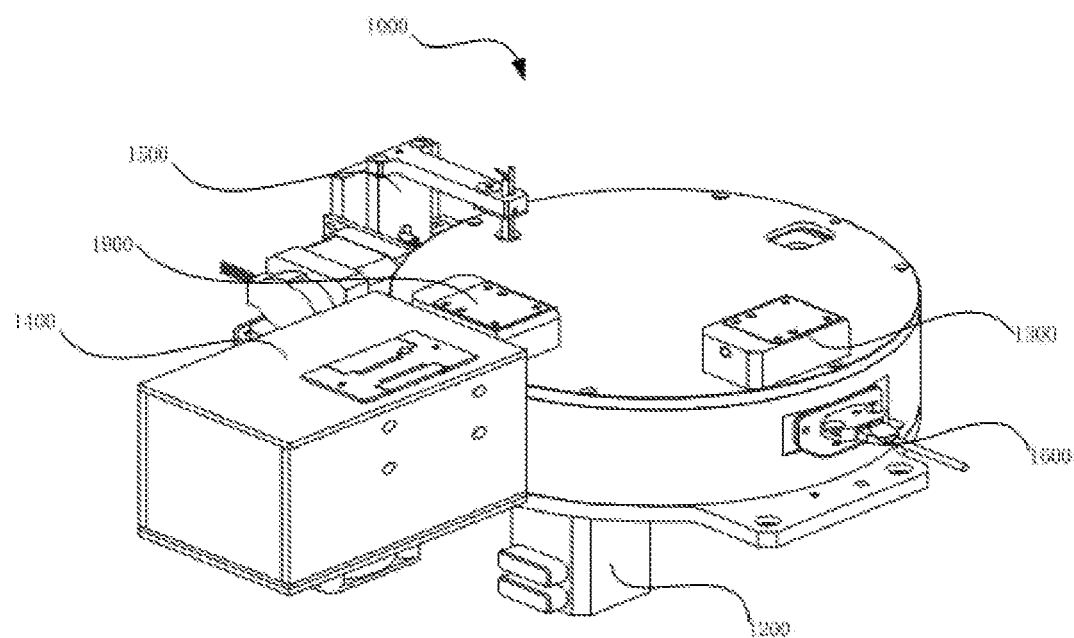
FIG. 1 is a structural schematic diagram of a measuring chamber in an embodiment.
Figure 2:
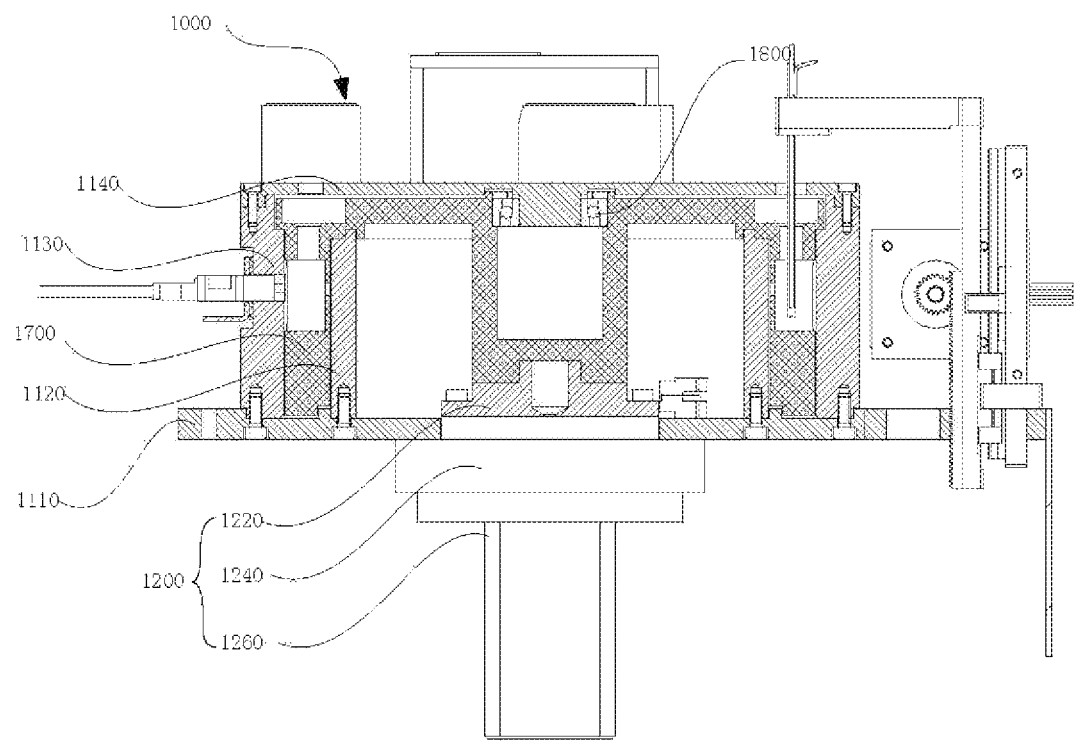
FIG. 2 is a sectional diagram of the measuring chamber of FIG. 1.
Figure 9:
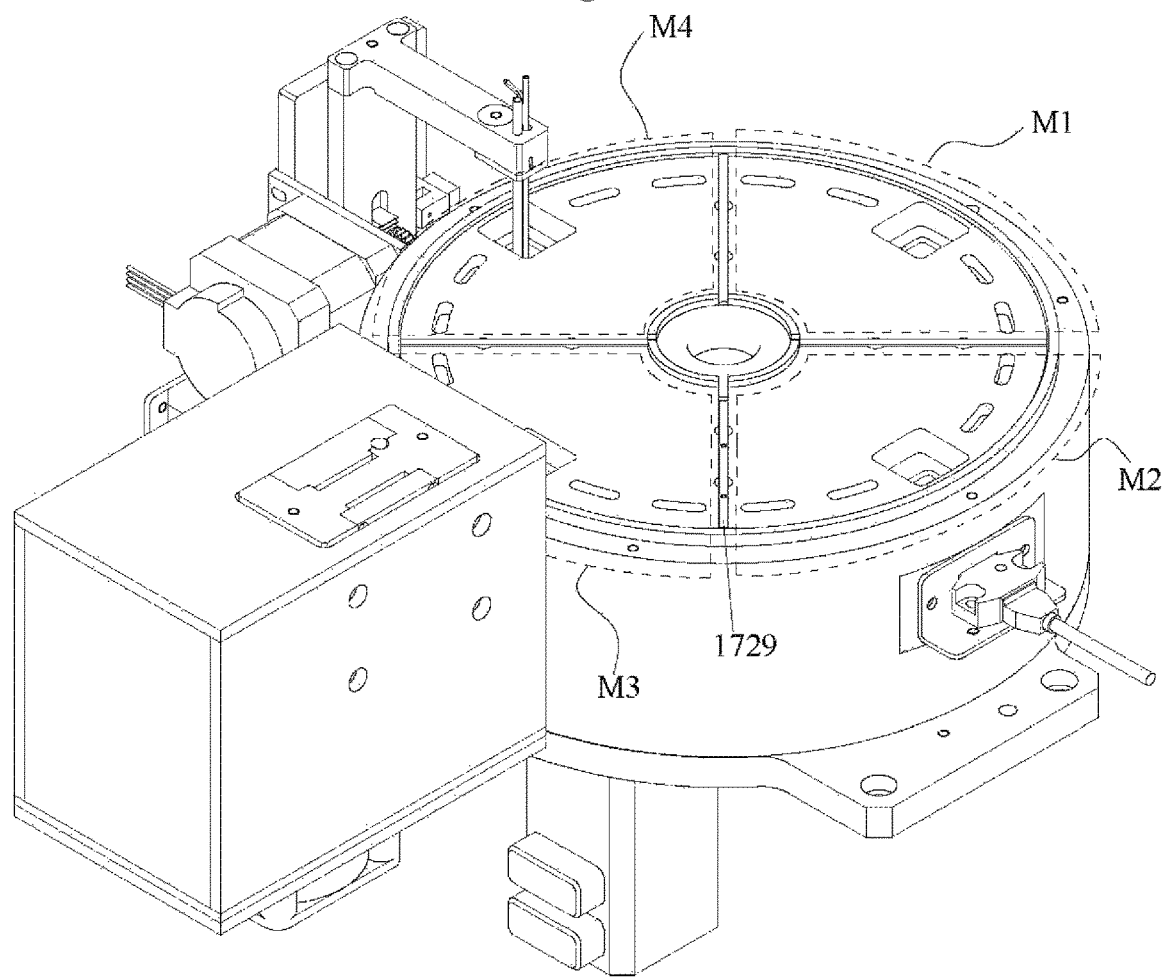
FIG. 9 is a structural schematic diagram of a first reaction cup processing, station, a second reaction cup processing station, a third reaction cup processing station and a fourth reaction cup processing station of the measuring chamber of FIG. 2.

With reference to FIG. 1, FIG. 2 and FIG. 9, a measuring chamber 1000 in one embodiment includes a bottom plate 1110, an inner shell 1120, an outer shell 1130, an upper cover 1140, a reaction cup turntable 1700, a driving mechanism 1200, a first substrate nozzle 1300, a second substrate nozzle 1900, a photomultiplier detection component 1400 and a waste liquor adsorption needle component 1500. The bottom plate 1110, the outer shell 1130 and the upper cover 1140 are enclosed into a holding space (not shown in the figure) of the measuring chamber 1000. The reaction cup turntable 1700 and the inner shell 1120 are located in the holding space. The bottom plate 1110, the outer shell 1130, the inner shell 1120, the upper cover 1140 and the reaction cup turntable 1700 are formed into a dark chamber (not shown in the figure). The measuring chamber 1000 includes four reaction cup processing stations sealed in a mutually light-isolated manner;

a first reaction cup processing station M1 (a reaction cup entering station), a reaction cup being placed into or taken out of the measuring chamber 1000 at the first reaction cup processing station M1;

a second reaction cup processing station M2 (an excitation substrate I adding station), a first substrate nozzle 1300 being placed at the second reaction cup processing station M2 so as to add an excitation substrate I to the reaction cup;

a third reaction cup processing station M3 (a reaction cup measuring station), a second substrate nozzle 1900 being arranged at the third reaction cup processing station M3 so as to add an excitation substrate II to the reaction cup and a photomultiplier detection component 1400 being arranged at the third reaction cup processing station M3; and a fourth reaction cup processing station M4 (a waste liquor extracting station), a waste liquor adsorption needle component 1500 being arranged at the fourth reaction cup processing station M4 so as to extract waste liquor of the reaction cup.

The first reaction cup processing station M1, the second reaction cup processing station M2, the third reaction cup processing station M3 and the fourth reaction cup processing station M4 are arranged sequentially along a rotation direction of the reaction cup turntable 1700 and are sealed in a mutually light-isolated manner; the first reaction cup processing station M1 and the third reaction cup processing station M3 are arranged diagonally; and the second reaction cup processing station M2 and the fourth reaction cup processing station M4 are arranged diagonally.

Figure 3:
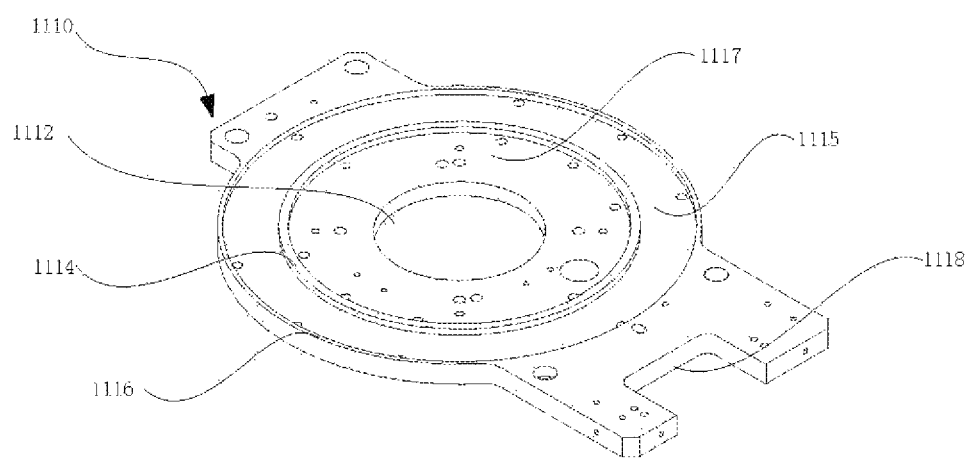
FIG. 3 is a structural schematic diagram of a bottom plate of the measuring chamber of FIG. 2.

With reference to FIG. 3, in one embodiment, a first through hole 1112 is formed on the bottom plate 1110. The bottom plate 1110 is formed into a fourth annular lug boss 1116 and a fifth annular lug boss 1114 sequentially and inward along a radial direction of the first through hole 1112. The fourth annular lug boss 1116 is formed by stretching the outer edge of the bottom plate 1110 convexly upward. Central axial lines of the fifth annular lug boss 1114, the fourth annular lug boss 1116, the first through hole 1112 and the reaction cup turntable 1700 are the same. The inner diameter of the fifth annular lug boss 1114 is smaller than that of the fourth annular lug boss 1116. A first holding groove 1115 is formed between the fourth annular lug boss 1116 and the fifth annular lug boss 1114. A second holding groove 1117 is formed between the fifth annular lug boss 1114 and the first through hole 1112. An opening 1118 is further formed on the bottom plate 1110. The opening 1118 is configured to mount the waste liquor adsorption needle component 1500.

Figure 4:
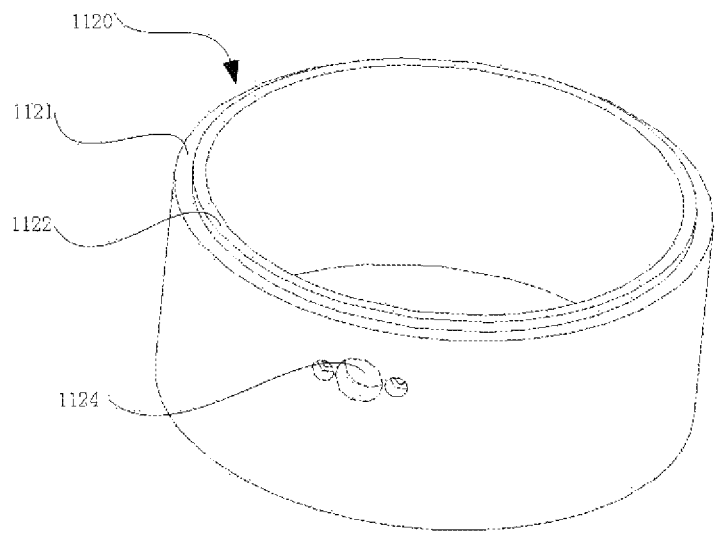
FIG. 4 is a structural schematic diagram of an inner shell of the measuring chamber of FIG. 2.

With reference to FIG. 4, in one embodiment, the inner shell 1120 is of a cylindrical shape. An annular groove 1121 is formed at the top outer edge of the inner shell 1120, thereby forming a second annular lug boss 1122 on the top of the inner shell 1120 (that is, the second annular lug boss 1122 is located at one end, close to the reaction cup turntable 1700, of the inner shell 1120). A second through hole 1124 is formed on the inner shell 1120. A light source is mounted on the inner wall of the inner shell 1120 and corresponding to the second through hole 1124. The second through hole 1124 is configured to pass through light emitted by the light source.

Figure 5:
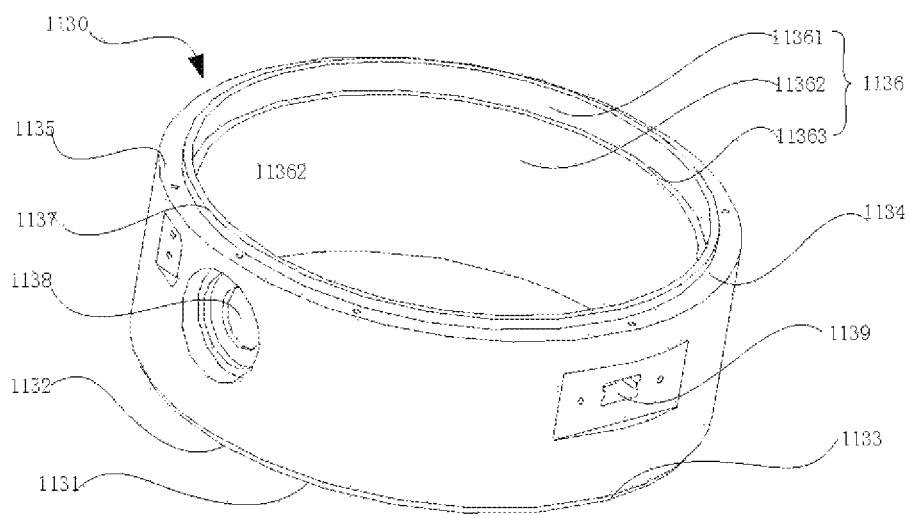
FIG. 5 is a structural schematic diagram of an outer shell of the measuring chamber of FIG. 2.

With reference to FIG. 5, in one embodiment, the outer shell 1130 is of a cylindrical shape. A fourth annular groove 1132 is formed at the bottom outer edge of the outer shell 1130, thereby forming a first neck portion 1131 and a first shoulder portion 1133 at the bottom of the outer shell. A third annular groove 1134 is formed at the top outer edge of the outer shell 1130, thereby forming a third neck portion 1137 and a third shoulder portion 1135 on the top of the outer shell. An inner cavity of the outer shell 1130 is a step hole 1136. The step hole 1136 includes a first hole 11361 and a second hole 11362. The first hole 11361 and the second hole 11362 are respectively located at the top end and the bottom end of the outer shell 1130. The diameter of the first hole 11361 is greater than that of the second hole 11362, thereby forming, a first annular groove 11363 at the intersection of the first hole 11361 and the second hole 11362.

In some embodiments, a third through hole 1138 is formed on the sidewall of the outer shell 1130. Meanwhile, with reference to FIG. 1, the outer shell 1130 is provided with a photomultiplier detection component 1400 corresponding to the third through hole 1138. The photomultiplier detection component 1400 detects the number of photons produced by chemiluminescence immunoreaction in the dark chamber (not shown in the figure) via the third through hole 1138. A fourth through hole 1139 for mounting an optocoupler 1600 is further formed on the outer shell 1130. The optocoupler 1600 is configured to detect whether there are the reaction cup at the second reaction cup processing station M2 or not in the dark chamber (not shown in the figure).

Figure 6:
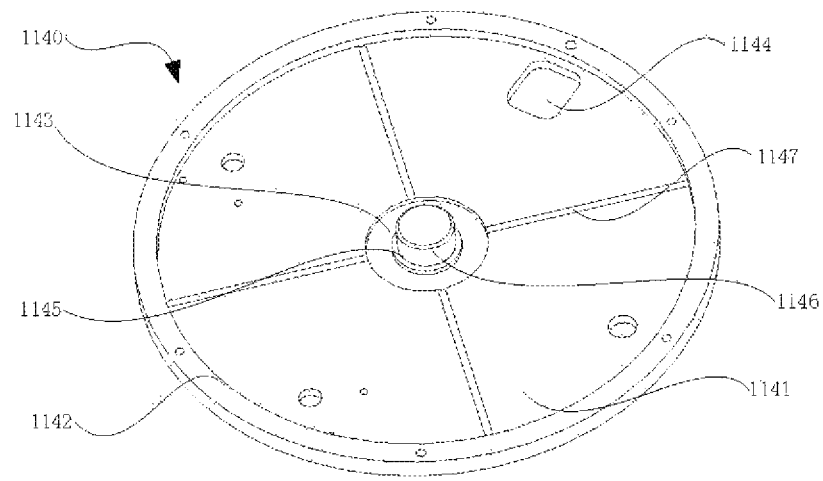
FIG. 6 is a structural schematic diagram of an upper cover of the measuring chamber of FIG. 2.

With reference to FIG. 6, in one embodiment, the upper cover 1140 includes a circular cover plate 1141 and a third annular lug boss 1142. The outer edge of the cover plate 1141 is stretched convexly and downward to form the third annular lug boss 1142. The third annular lug boss 1142 surrounds a central axial line of the cover plate 1141. The cover plate 1141 includes a first surface (namely, a bottom surface of the cover plate) and a second surface (namely, a top surface of the cover plate) arranged oppositely, in which the first surface is located at the bottom and the second surface is located on the top. A first blind hole 1143 is formed in the center of the first surface of the cover plate 1141. A first cylinder 1145 and a second cylinder 1146 are formed by protruding the center of a bottom surface of the first blind hole 1143 sequentially and downward. The first cylinder 1145 is close to the bottom surface of the first blind hole 1143, and the second cylinder 1146 is far away from the bottom surface of the first blind hole 1143. The diameter of the first cylinder 1145 is greater than that of the second cylinder 1146. Central axial lines of the first cylinder 1145, the second cylinder 1146, the first blind hole 1143 and the cover plate 1141 are a same axial line. Four second light-isolated component holding grooves 1147 symmetrically distributed along the periphery of the cover plate 1141 are formed on the first surface of the cover plate 1141. The second light-isolated component holding grooves 1147 are extended along a radial direction of the first surface and are connected between the first blind hole 1143 and a third annular lug boss 1142. The four second light-isolated component holding grooves 1147 are symmetrically distributed relative to a central axial line of the third annular lug boss 1142, thus dividing the cover plate 1141 into four areas. In some embodiments, a reaction in-out port 1144 is further formed on the upper cover 1140.

Figure 7:
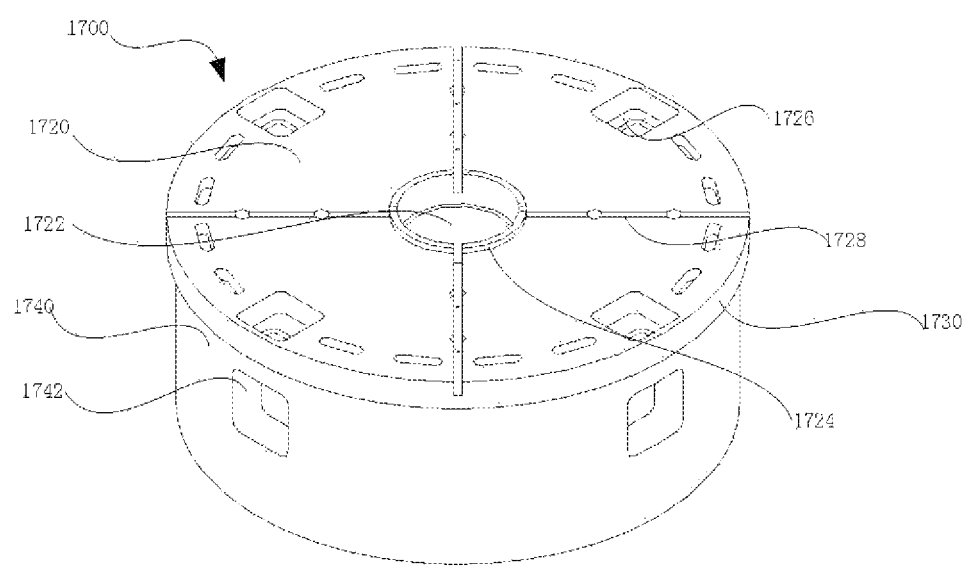
FIG. 7 is a structural schematic diagram of a direction of a reaction cup turntable of the measuring chamber of FIG. 2.
Figure 8:
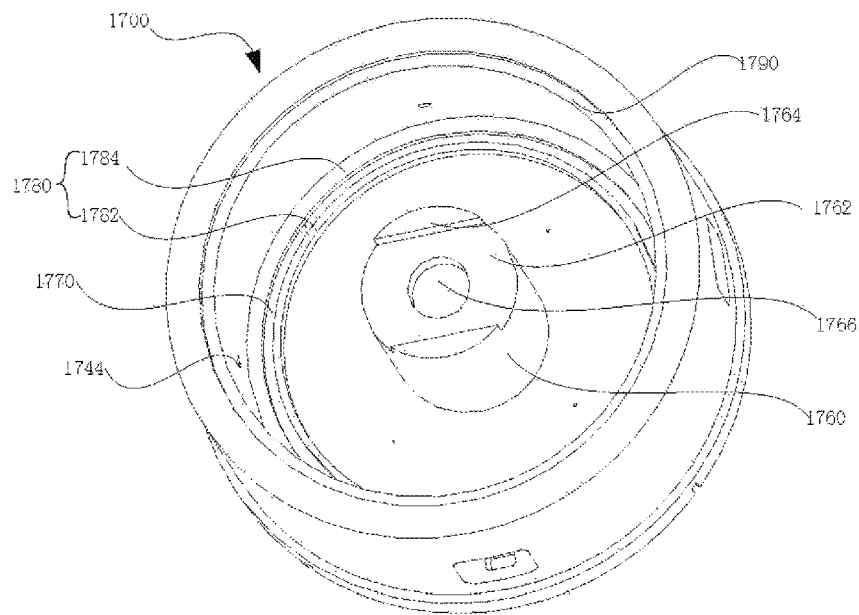
FIG. 8 is a structural schematic diagram of another direction of a reaction cup turntable of the measuring chamber of FIG. 2.

With reference to FIG. 7 and FIG. 8, in one embodiment, the reaction cup turntable 1700 is arranged between the inner shell 1120 and the outer shell 1130 along a radial direction of the reaction cup turntable 1700, and the reaction cup turntable 1700 is located between the upper cover 1140 and the bottom plate 1110 along an axial direction of the reaction cup turntable 1700. The reaction cup turntable 1700 includes a top plate 1720, a peripheral wall 1740 and a rotating shaft 1760. The top plate 1720 is of a disk shape and includes a first surface and a second surface arranged oppositely, in which the first surface is located at the bottom, the second surface is located on the top and the second surface is in clearance fit with the upper cover 1140.

In some embodiments, the peripheral wall 1740 is of a cylindrical shape overall, and is formed by extending the first surface of the top plate 1720 vertically and downward. The peripheral wall 1740 is surrounded to form an inner cavity of the reaction cup turntable 1700. The diameter of the top plate 1720 is greater than the outer diameter of the peripheral wall 1740, so that the top plate 1720 is stretched convexly and outward along a radial direction relative to the peripheral wall 1740 to form a first annular lug boss 1730. The peripheral wall 1740 includes a first end and a second end, in which the first end is close to the first surface of the top plate 1720 and the second end is far away from the first surface of the top plate 1720. A fifth annular groove 1790 is formed inside the second end of the peripheral wall 1740 (the bottom surface of the peripheral wall). The fifth annular groove 1790 surrounds a rotation central axial line of the reaction cup turntable.

In some embodiments, the rotating shaft 1760 is formed by extending the center of the first surface of the top plate 1720 vertically and downward. The rotating shaft 1760 includes a first end and a second end, in which the first end is close to the first surface of the top plate 1720 and the second end is far away from the first surface of the top plate 1720. A notched groove 1762 is formed on the second end of the rotating shaft 1760. The notched groove 1762 is penetrated through the second end of the rotating shaft 1760 along a horizontal direction and is formed into two bumps 1764 arranged oppositely. The two bumps 1764 are respectively and symmetrically arranged at both sides of the notched groove 1762. A second blind hole 1766 is formed on the top surface of the notched groove 1762. The central axial line of the second blind hole 1766 is the same as that of the rotating shaft 1760.

In some embodiments the first surface of the top plate 1720 is extended downward along the inner edge of the peripheral wall 1740 to form a first annular truncated cone 1780. The height of the first annular truncated cone 1780 is smaller than that of the peripheral wall 1740. The first annular truncated cone 1780 surrounds the central axial line of the reaction cup turntable 1700. The first annular truncated cone 1780 includes a first end and a second end arranged oppositely, in which the first end is close to the first surface of the top plate 1720 and the second end is far away from the first surface of the top plate 1720. A second annular groove 1770 is formed at the second end (a bottom surface of the first annular truncated cone) of the first annular truncated cone 1780 along the periphery of the first annular truncated cone 1780, thereby dividing the first annular truncated cone 1780 into a first portion 1782 and a second portion 1784. The first portion 1782 and the second portion 1784 respectively are of a circular ring shape and respectively surround a rotation central axial line of the reaction cup turntable 1700. The second portion 1784 is located at the radial outside of the first portion 1782.

In some embodiments, a step hole 1722 is formed in the center of the second surface of the top plate 1720. The step hole 1722 includes a big hole and a small hole, in which the big hole is located above the small hole and a step surface is formed at the junction of the big hole and the small hole. The step surface is of an annular shape and surrounds the rotation central axial line of the reaction cup turntable 1700. The second surface is extended convexly and upward at the periphery of the big hole to form a second, annular truncated cone 1724. The second annular truncated cone 1724 is of a circular ring shape and surrounds the central axial line of the reaction cup turntable 1700. Four reaction cup holding cavities 1726 are formed on the second surface and are configured to hold the reaction cups. Four measuring windows 1742 are formed on the outer surface of the peripheral wall 1740 of the reaction cup turntable 1700. The four measuring windows 1742 are in one-to-one correspondence and communicate with the four reaction cup holding cavities 1726. A light hole 1744 is formed on the inner surface of the peripheral wall 1740 of the reaction cup turntable 1700. The light hole 1744 communicate with the measuring window 1742. The light hole 1744 communicate with the inner cavity and the measuring window 1742 of the reaction cup turntable 1700. When a head of the reaction cup is suspended in the reaction cup holding cavity 1726, a cup body of the reaction cup is stretched into the measuring window 1742, so that the cup body of the reaction cup may be observed. Four first light-isolated component holding grooves 1728 are formed on the second surface. The first light-isolated component holding grooves 1728 are extended along a radial direction of the top plate 1720 and are connected between the big hole and the outer edge of the top plate 1720. The four first light-isolated component holding grooves 1728 are symmetrically distributed relative to the rotation central axial line of the reaction cup turntable 1700, thereby dividing the top plate 1720 into four reaction cup holding areas. Correspondingly, the reaction cup turntable 1700 is divided into four reaction cup holding areas, and each reaction cup holding area is correspondingly provided with one reaction cup holding cavity 1726. The four first light-isolated component holding grooves 1728, the four second light-isolated component holding grooves 1147, the four light-isolated components, the four reaction cup processing stations and the four reaction cup holding areas are in one-to-one correspondence in number. When the reaction cup turntable 1700 is rotated so as to rotate the four reaction cup holding areas to corresponding reaction cup processing stations, the four first light-isolated component holding grooves 1728 and the four second light-isolated component holding grooves 1147 are in one-to-one correspondence, and each of the second light-isolated component holding grooves 1147 and the corresponding first light-isolated component holding groove 1728 are jointly formed into a space for holding the light-isolated components.

With reference to FIG. 2-4, in one embodiment, the inner shell 1120 is arranged in the holding space (not shown in the figure) of the measuring chamber. The inner shell 1120 is fixedly mounted in the second holding groove 1117 of the bottom plate 1110, and the outer wall of the inner shell 1120 is abutted against one side, close to the first through hole 1112, of the fifth annular lug boss 1114 of the bottom plate 1110. The inner shell 1120 is located in the inner cavity of the reaction cup turntable 1700. The inner shell 1120 is located between the first surface of the top plate 1720 of the reaction cup turntable 1700 and the bottom plate 1110 along an axial direction.

Meanwhile, referring to FIG. 8, the second annular lug, boss 1122 is located at one end, close to the reaction cup turntable 1700, of the inner shell 1120. The first surface of the top plate of the reaction cup turntable 1700 is protruded to form the first annular truncated cone 1780. The second annular groove 1770 is formed peripherally on the first annular truncated cone 1780. The second annular lug boss 1122 of the inner shell 1120 is matched with the second annular groove 1770 of the reaction cup turntable 1700. The second annular lug boss 1122 is embedded into the second annular groove 1770 to form a second labyrinth structure. When the reaction cup turntable is rotated, the second annular lug boss 1122 may be slid relative to the second annular groove 1770. The inner shell 1120 is mounted in the inner cavity of the reaction cup turntable 1700, and a certain space is formed between the outer wall of the inner shell 1120 and the inner wall of the peripheral wall 1740 of the reaction cup turntable 1700. The space can meet the rotation of the reaction cup turntable 1700 in the dark chamber (not shown in the figure). In other embodiments the second annular lug boss 1122 may be an annular groove, and the second annular groove 1770 matched with the second annular lug boss 1122 may be an annular lug boss, as long as the second annular lug boss 1122 and the second annular groove 1770 may form a labyrinth zigzag surface.

With reference to FIG. 3 and FIG. 5, in one embodiment, the outer shell 1130 is fixed mounted on the first holding groove 1115 of the bottom plate 1110; the fourth annular groove 1132 of the outer shell 1130 is located at one end, close to the bottom plate 1110, of the outer shell 1130; the fourth annular groove 1132 is matched with the fourth annular lug boss 1116 of the bottom plate 1110; the first neck portion 1131 of the outer shell 1130 is abutted against the side, close to the first holding groove 1115, of the fourth annular lug boss 1116, and the first shoulder portion 1133 is erected on the top surface of the fourth annular lug boss 1116 thereby forming a fourth labyrinth structure. In other embodiments, the fourth annular lug boss 1116 may be an annular groove, and the fourth annular groove 1132 matched with the fourth annular lug, boss 1116 may be an annular lug boss, as long as the fourth annular lug boss 1116 and the fourth annular groove 1132 may form a labyrinth zigzag surface. In some embodiments, the third through hole 1138 on the outer shell 1130 is corresponding to the second through hole 1124 on the inner shell 1120. The third through hole 1138 and the second through hole 1124 have the same central axial line. When the reaction cup turntable 1700 conveys the reaction cup to the third reaction cup processing station M3, the third through hole 1138 and the second through hole 1124 communicate with the light hole 1744 and the measuring window 1742 on the reaction cup turntable 1700.

With reference to FIG. 5 and FIG. 6, in one embodiment, the upper cover 1140 is fixedly mounted on the outer shell 1130; the side, close to the central axial line of the upper cover 1140, of the third annular lug boss 1142 is abutted against the third neck portion 1137 of the outer shell 1130, and the bottom surface of the third annular lug boss 1142 is erected on the third shoulder portion 1135, so that the third annular lug boss 1142 is matched with the third annular groove 1134, thereby forming a third labyrinth structure. In other words, the outer edge of the cover plate 1141 is stretched convexly to form the third annular lug boss 1142; the third annular groove 1134 is located at one end, close to the upper cover 1140, of the outer shell 1130, and the third annular lug boss 1142 is matched with and abutted against the third annular groove 1134 to form the third labyrinth structure. In other embodiments, the third annular lug boss 1142 may be an annular groove, and the third annular groove 1134 matched with the third annular lug boss 1142 may be an annular lug boss, as long as the third annular lug boss 1142 and the third annular groove 1134 may form a labyrinth zigzag surface.

With reference to FIG. 2, FIG. 5 and FIG. 7, in one embodiment, the first annular lug boss 1730 of the reaction cup turntable 1700 is matched with the first annular groove 11363 of the outer shell 1130 to form a first labyrinth. A certain space is formed between a side of the first annular lug boss 1730 and a wall of the first hole 11361, and the space can meet the rotation of the reaction cup turntable 1700 in the holding space (not, shown in the figure) of the measuring chamber. The bottom surface of the first annular lug boss 1730 is abutted against the bottom surface of the first annular groove 11363, so when the reaction cup turntable 1700 is rotated, the first annular lug boss 1730 may be slid relative to the first annular groove 11363. In other words, the top plate 1720 of the reaction cup turntable 1700 is stretched convexly and outward along the radial direction to form the first annular lug boss 1730, the first annular groove 11363 is formed at the junction of the first hole and the second hole of the outer shell 1130, and the first annular lug boss 1730 is embedded into the first annular groove 11363 and can be slid relative to the first annular groove 11363, thereby forming the first labyrinth structure. In other embodiments, the first annular lug boss 1730 may be an annular groove, and the first annular groove 11363 matched with the first annular lug boss 1730 may be an annular lug boss, as long as the first annular lug boss 1730 and the first annular groove 11363 may form a labyrinth zigzag surface. The peripheral wall 1740 of the reaction cup turntable 1700 is arranged in a space enclosed by the bottom plate 1110, the inner shell 1120 and the outer shell 1130, and a certain space is formed between the second end of the peripheral wall 1740 and the bottom plate 1110, and the space can meet the rotation of the reaction cup turntable 1700 in the holding space (not shown in the figure) of the measuring chamber.

With reference to FIG. 4 and FIG. 8, in one embodiment, the fifth annular groove 1790 on the peripheral wall 1740 is matched with the fifth annular lug boss 1114 on the bottom plate 1110 to form a fifth labyrinth structure, and when the reaction cup turntable 1700 is rotated, the fifth annular groove 1790 may be slid relative to the fifth annular lug boss 1114. In other embodiments, the fifth annular lug boss 1114 may be an annular groove, and the fifth annular groove 1790 matched with the fifth annular lug boss 1114 may be an annular lug boss, as long as the fifth annular lug boss 1114 and the fifth annular groove 1790 may form a labyrinth zigzag surface.

With reference to FIG. 2, FIG. 6 and FIG. 7, in one embodiment, the second annular truncated cone 1724 of the reaction cup turntable 1700 is arranged in the first blind hole on the upper cover 1140 in, a sleeving manner. The side, far away from the central axial line of the reaction cup turntable 1700, of the second annular truncated cone 1724 is abutted against the wall of the first blind hole 1143. The top surface of the second annular truncated cone 1724 is abutted against the bottom surface of the first blind hole 1143. The step hole 1722 is configured to mount a bearing 1800. The bearing 1800 is arranged in the big hole of the step hole 1722, and is supported on the step, surface formed by the big hole and the small hole. The second cylinder 1146 of the upper cover 1140 is stretched into the step hole 1722, and is arranged in the bearing 1800 in a sleeving manner. A limit step is formed at the junction of the first cylinder 1145 and the second cylinder 1146 of the upper cover 1140 so as to limit the bearing 1800. In other words, the bearing 1800 is axially limited between the limit step and the step surface.

In some embodiments, each of the light-isolated components (omitted in the figure) includes an elastic element 1729 and a light-isolated plate. The elastic element 1729 is fixedly connected to the first light-isolated component holding groove 1728 via a bolt and the light-isolated plate is placed on the elastic element 1729. When the reaction cup turntable 1700 is rotated till the position of the second light-isolated component holding groove 1147 is completely overlapped with that of the first light-isolated component holding groove 1728, the elastic element 1729 is in an upspring state. Through the elastic element 1729, the light-isolated plate is abutted into the second light-isolated component holding groove 1147. The light-isolated component (omitted in the figure) is located in a light-isolated component holding cavity formed by the second light-isolated component holding groove 1147 and the corresponding first light-isolated component holding groove 1728, so that the upper cover 1140 and the reaction cup turntable 1700 are sealed; and when the reaction cup on the reaction cup turntable 1700 is located at the reaction cup processing station, the corresponding reaction cup processing may be performed. When the reaction cup turntable 1700 is rotated till the position of the first light-isolated component holding groove 1728 is staggered with that of the second light-isolated component holding groove 1147, the elastic element 1729 is in a compressed state, and the upper cover 1140 presses the light-isolated plate (omitted in the figure) into the first light-isolated component holding groove 1728, so that the upper cover 1140 and the reaction cup turntable 1700 may be in relative rotation.

With reference to FIG. 2, in one embodiment, the driving mechanism 1200 is fixedly mounted on the bottom plate 1110 via the first through hole on the bottom plate 1110. The driving mechanism 1200 includes a connection block 1220, a rotary platform 1240 and a motor 1260. The connection block 1220 is fixedly connected with the rotary platform 1240, for example, via a bolt. The motor 1260 is fixedly connected to the rotary platform 1240. The motor 1260 drives the rotary platform 1240 to rotate. The connection block 1220 is clamped with the notched groove 1762 of the reaction cup turntable 1700. When the rotary platform 1240 is rotated, the connection block 1220 fixedly connected with the rotary platform 1240 is driven to move, thus driving the reaction cup turntable 1700 connected with the connection block 1220 to move and implementing the effect that the driving mechanism 1200 drives the reaction cup turntable 1700 to rotate in the dark chamber.

In one embodiment, the photomultiplier detection component 1400 is mounted on the outer shell 1130, is arranged at the third reaction cup processing station M3 and opposite to the reaction cup in-out port 1144 and is configured to detect the number of photons produced by chemiluminescence immunoreaction in the dark chamber (not labeled in the figure). The upper cover 1140 is provided with two substrate nozzles for adding an excitation substrate to a to-be-tested reaction cup. The first substrate nozzle 1300 corresponding to the optocoupler 1600 is mounted on the upper cover 1140 and is located at the second reaction cup processing station M2. The second substrate nozzle 1900 corresponding to the photomultiplier detection component 1400 is mounted on the upper cover 1140 and is located at the third reaction cup processing station M3. The first substrate nozzle 1300 and the second substrate nozzle 1900 are arranged on the upper cover 1140 in a right-angled manner. The measuring chamber 1000 includes the waste liquor adsorption needle component 1500 and the optocoupler 1600. The waste liquor adsorption needle component 1500 is mounted on the bottom plate 1110, is located at the fourth reaction cup processing station M4, and is configured to extract away the waste liquor in a detected reaction cup. The optocoupler 1600 is mounted on the outer shell 1130 of the dark chamber (not labeled in the figure) and is configured to detect whether there is the reaction cup at the second reaction cup processing station M2 or not in the dark chamber.

In some embodiments, the measuring chamber of the present disclosure includes a grounding component (not labeled in the figure) made of a metal material. The grounding component is mounted in the second holding groove 1117 of the bottom plate 1110 and is located in the inner cavity of the reaction cup turntable 1700. A certain distance is formed between the top of the grounding component and the upper cover 1140. An elastic piece capable of being bent elastically and downward is arranged on the top of the grounding component. The elastic piece is pre-pressed between the top plate 1720 of the reaction cup turntable 1700 and the grounding component. During rotation of the reaction cup turntable 1700, a static electricity is generated and the grounding component is configured to release the static electricity, thereby preventing the influence on the work of the measuring chamber 1000.

Figure 10:
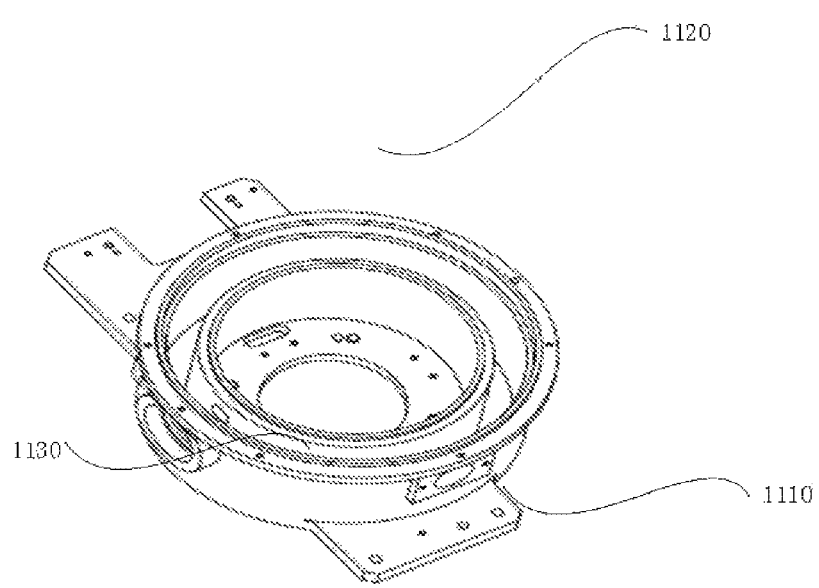
FIG. 10 is a schematic diagram of a fixed and integrated structure of a bottom plate, an inner shell and an outer shell of a measuring chamber in another embodiment.

In another embodiment, as shown in FIG. 10, the bottom plate 1110, the outer shell 1130 and the inner shell 1120 of the measuring chamber 1000 are fixed and integrated together. The upper cover 1140 is fixed on the outer shell 1130. The first labyrinth structure is formed at the junction of the top of the outer shell 1130 and the reaction cup turntable 1700. The second labyrinth structure is formed at the junction of the top of the inner shell 1120 and the reaction cup turntable 1700. In some embodiments, the third labyrinth structure is formed at the junction of the outer shell 1130 and the upper cover 1140. The measuring chamber, the first labyrinth structure, the second labyrinth structure and the third labyrinth structure are as described above and will not be repeated here.

In some embodiments, the parallel working method for the multiple reaction cup processing stations of the measuring chamber 1000 includes the following steps.

1) A first reaction cup loaded with a to-be-tested sample is placed into a first reaction cup holding cavity 1726 of a reaction cup turntable 1700 at a first reaction cup processing station M1 through a reaction cup in-out port 1144 of an upper cover 1140.

2) A driving mechanism 1200 drives the reaction cup turntable 1700 to rotate 90°, so that the first reaction cup holding cavity 1726 is moved to a second reaction cup processing station M2 and a second reaction cup holding cavity 1726 is moved to the first reaction cup processing station M1, and then the following steps are executed synchronously.

(1) An optocoupler 1600 detects that there is the reaction cup on the reaction cup turntable 1700 and a first substrate nozzle 1300 adds an excitation substrate I to the first reaction cup at the second reaction cup processing station M2.

(2) A second reaction cup is placed into the second reaction cup holding cavity 1726 at the first reaction cup processing station M1.

3) The driving mechanism 1200 drives the reaction cup turntable 1700 to rotate 90°, so that the first reaction cup holding cavity 1726 is moved to a third reaction cup processing station M3, the second reaction cup holding cavity 1726 is moved to the second reaction cup processing station M2 and a third reaction cup holding cavity 1726 is moved to the first reaction cup processing station M1, and then the following steps are executed synchronously.

(1) A second substrate nozzle 1900 adds an excitation substrate II to the first reaction cup, and under the action of the excitation substrate II, when a specific substance in the to-be-tested sample emits light, a photomultiplier detection component 1400 receives and records the number of photons for detection.

(2) The first substrate nozzle 1300 adds the excitation substrate I to the second reaction cup.

(3) A third reaction cup is placed into the third reaction cup holding cavity 1726 at the first reaction cup processing station M1.

4) The driving mechanism 1200 drives the reaction cup turntable 1700 to rotate 90°, so that the first reaction cup holding cavity 1726 is moved to a fourth reaction cup processing station M4, the second reaction cup holding cavity 1726 is moved to the third reaction cup processing station M3, the third reaction cup holding cavity 1726 is moved to the second reaction cup processing station M2 and a fourth reaction cup holding cavity 1726 is moved to the first reaction cup processing station M1, and then the following steps are executed synchronously.

(1) A waste liquor adsorption needle component 1500 extracts away waste liquor in the first reaction cup detected.

(2) The second substrate nozzle 1900 adds the excitation substrate II to the second reaction cup, and under the action of the excitation substrate II, when the specific substance in the to-be-tested sample emits the light, the photomultiplier detection component 1400 receives and records the number of photons for detection.
  (3) The first substrate nozzle 1300 adds the excitation substrate I to the third reaction cup.
  (4) A fourth reaction cup is placed into the fourth reaction cup holding cavity 1726 at the first reaction cup processing station M1.

5) The driving mechanism 1200 drives the reaction cup turntable 1700 to rotate 90° so that the first reaction cup holding cavity 1726 is moved to the first reaction cup processing station M1, the second reaction cup holding cavity 1726 is moved to the fourth reaction cup processing station M4, the third reaction cup holding cavity 1726 is moved to the third reaction cup processing station M3 and the fourth reaction cup holding cavity 1726 is moved to the second reaction cup processing station M2, and then the following steps are executed synchronously.
  (1) The first reaction cup is taken out and a fifth reaction cup is placed into at the first reaction cup processing station M1.
  (2) The waste liquor adsorption needle component 1500 extracts away waste liquor in the second reaction cup.
  (3) The second substrate nozzle 1900 adds the excitation substrate II to the third reaction cup, and under the action of the excitation substrate II, when the specific substance in the to-be-tested sample emits the light, the photomultiplier detection component 1400 receives and records the number of photons for detection.
  (4) The first substrate nozzle 1300 adds the excitation substrate I to the fourth reaction cup.

In some embodiments, the parallel working method for the multiple reaction cup processing stations of the measuring chamber 1000 includes the following steps.

S1: a first reaction cup loaded with a to-be-tested sample is placed into the measuring chamber 1000 at a reaction cup entering station.

S2: a photomultiplier detection component 1400 measures the number of photons of a second reaction cup at a reaction cup measuring station.

In some embodiments, the method includes the following step executed synchronously: a waste liquor adsorption needle component 1500 extracts away waste liquor in a third reaction cup, in which the number of photons is measured completely, at a waste liquor extraction station.

In some embodiments, the method includes the following step executed synchronously: a first substrate nozzle 1300 adds an excitation substrate I to a fourth reaction cup, in which the number of photons is to be measured, at an excitation substrate I adding station.

In some embodiments, in the step S2, it includes: a second substrate nozzle 1900 first adds an excitation substrate II to the second reaction cup.

In some embodiments, in the step S1, it includes: a fifth reaction cup in which the waste liquor is extracted is taken out of the measuring chamber 1000 first at the reaction cup entering station.

In some embodiments, the chemiluminescence measurement method of the measuring chamber 1000 includes the following steps.

1) a first reaction cup loaded with a to-be-tested sample is placed into a first reaction cup holding cavity of a reaction cup turntable 1700 at a first reaction cup processing station M1.
  2) The reaction cup turntable 1700 is rotated so as to move the first reaction cup holding cavity to a second reaction cup processing station M2, and a first substrate nozzle 1300 adds an excitation substrate I to the first reaction cup at the second reaction cup processing station M2.
  3) The reaction cup turntable 1700 is rotated so as to move the first reaction cup holding cavity to the third reaction cup processing station M3, a second substrate nozzle 1900 adds an excitation substrate II to the first reaction cup, and under the action of the excitation substrate II, when a specific substance in the to-be-tested sample emits light, a photomultiplier detection component 1400 receives and records the number of photons for detection.
  4) The reaction cup turntable 1700 is rotated so as to move the first reaction cup holding cavity to a fourth reaction cup processing station M4, and a waste liquor adsorption needle component 1500 extracts away waste liquor in the first reaction cup.
  5) The reaction cup turntable 1700 is rotated so as to move the first reaction cup holding cavity to the first reaction cup processing station M1, and the first reaction cup is taken out and a new reaction cup is placed into at the first reaction cup processing station M1.

The present disclosure further provides a chemiluminescence detector in one embodiment. The chemiluminescence detector includes the measuring chamber 1000 as shown in FIG. 1 to FIG. 8.

The measuring, chamber 1000 of the present disclosure is formed into a plurality of above zigzag labyrinth structures, for examples, a fourth labyrinth structure formed at the junction of a bottom plate 1110 and an outer shell 1130, a fifth labyrinth structure formed at the junction of the bottom plate 1110 and a reaction cup turntable 1700, a third labyrinth structure formed at the junction of the outer shell 1130 and an upper cover 1140, a first labyrinth structure formed at the junction of the outer shell 1130 and the reaction cup turntable 1700, and a second labyrinth structure formed at the junction of an inner shell 1120 and the reaction cup turntable 1700. When the outside natural light is irradiated to the measuring chamber 1000 and is transferred to a dark chamber (not labeled in the figure), through the reflection of a plurality of zigzag surfaces, the intensity of the natural light, is nearly eliminated or is reduced, and thus the influence of the natural light on the detection is eliminated and the accuracy of the detection result is improved.

In addition, the zigzag labyrinth structures of the present disclosure also have dynamic sealing effect, so that the problem of residual luminous interference due to the fact that the plurality of reaction cups are processed simultaneously in parallel in the measuring chamber 1000 in which multiple reaction cup processing stations are processed in parallel is solved. When a driving mechanism 1200 drives the reaction cup turntable 1700 to rotate in the dark chamber (not labeled in the figure), the reaction cups in the plurality of reaction cup holding cavities 1726 are simultaneously moved in the dark chamber (not labeled in the figure) with the reaction cup turntable 1700; and after the reaction cups are conveyed to corresponding processing stations for processing the reaction cups, the plurality of different processing stations for processing the reaction cups may simultaneously perform parallel processing on the reaction cups conveyed to the corresponding reaction cup processing stations, so that the measuring chamber implements simultaneous work of reaction cup in-out, excitation substrate adding, photon measurement and waste liquor disposal at the different reaction cup processing stations, and thus the measurement speed of the instrument is greatly improved.

Meanwhile, a plurality of light-isolated components of the present disclosure are arranged between the reaction cup turntable 1700 and the upper cover 1140. The plurality of light-isolated components can be rotated together with the reaction cup turntable 1700 relative to the upper cover 1140, so that the reaction cup turntable 1700 is divided into a plurality of reaction cup holding areas sealed in a mutually light-isolated manner. The light isolation effect among the plurality of reaction cup holding areas is relatively good, so during the parallel working process of the plurality of reaction cup processing stations of the measuring chamber, a plurality of reaction cups that work in parallel on each of the reaction cup processing stations have no light interference mutually; and particularly, the reaction cup at the third reaction cup processing station M3 (reaction cup measuring station) is not interfered by light rays produced by the reaction cups at the other reaction cup processing stations during measurement. Not only is the accuracy of the detection result improved, but also the problem of residual luminous interference due to the fact that a plurality of reaction cups in a same measuring chamber are processed simultaneously in parallel is solved; and therefore, the measuring chamber implements the simultaneous work of reaction cup in-out, excitation substrate adding, photon measurement and waste liquor disposal at the different reaction cup processing stations, and thus the measurement speed of the instrument is greatly improved.

Each technical characteristic of the above embodiments may be combined freely. To describe concisely, all possible combinations for the each technical characteristic of the above embodiments are not described. However, as long as there is no conflict among the combinations of these technical characteristics, all should be considered as a recording scope of the specification.

The above embodiments are only several embodiments of the present disclosure and are described concretely in detail, and therefore, should not be understood as limits to scope of the present disclosure. It should be noted that, those of ordinary skill in the art further may make several alternations and improvements without departing from the concept of the present disclosure, and all should pertain to the scope of protection of the present disclosure. Therefore, the scope of protection of the present disclosure should be subjected to the appended claims.

What is claimed is:

1. A measuring chamber for processing multiple reaction cup processing stations in parallel, comprising: a dark chamber, a first substrate nozzle, a photomultiplier detection component, a waste liquor adsorption needle component, a reaction cup turntable and a plurality of reaction cup processing stations, the reaction cup turntable being provided in the measuring chamber rotationally, wherein the plurality of reaction cup processing stations are sealed in a mutually light-isolated manner,
   an upper cover, wherein the reaction cup turntable comprises a top plate and a peripheral wall;
   the upper cover is provided above the top plate; the top plate comprises a first surface and a second surface arranged oppositely;
   the peripheral wall is provided on the first surface;
   the peripheral wall surrounds a central axial line of the reaction cup turntable so as to form an inner cavity of the reaction cup turntable;
   the second surface is toward the upper cover;
   the second surface is in a clearance fit with the upper cover;
   a plurality of first light-isolated component holding grooves are formed on the second surface and extend along a radial direction from a central region of the second surface to an outer edge of the top plate;
   each of the first light-isolated component holding grooves is provided with a light-isolated component inside; and
   the light-isolated component is elastically clamped between the first light-isolated component holding groove and the upper cover.

2. The measuring chamber as claimed in claim 1, further comprising a bottom plate, an inner shell, and an outer shell, wherein the bottom plate, the outer shell and the upper cover are enclosed into a holding space; the reaction cup turntable and the inner shell are provided in the holding space; the reaction cup turntable is provided between the inner shell and the outer shell along a radial direction; the reaction cup turntable is provided between the upper cover and the bottom plate along an axial direction; and the bottom plate, the outer shell, the inner shell, the reaction cup turntable and the upper cover are formed into the dark chamber.

3. The measuring chamber as claimed in claim 1, wherein the reaction cup turntable comprises a plurality of reaction cup holding areas; a plurality of second light-isolated component holding grooves are formed on a cover plate of the upper cover; the plurality of second light-isolated component holding grooves are in one-to-one correspondence with the plurality of first light-isolated component holding grooves; and when each of the reaction cup holding areas is rotated to corresponding reaction cup processing station, the second light-isolated component holding grooves and the first light-isolated component holding grooves are in one-to-one correspondence to form spaces for holding the light-isolated components.

4. The measuring chamber as claimed in claim 3, wherein the plurality of second light-isolated component holding grooves, the plurality of first light-isolated component holding grooves, the plurality of reaction cup holding areas and the plurality of reaction cup processing stations are in one-to-one correspondence in number; each of the light-isolated components comprises an elastic element and a light-isolated plate; the elastic element is held in the first light-isolated component holding groove; and when the reaction cup turntable is rotated, the light-isolated plate is abutted against a bottom plate of the upper cover or into the second light-isolated component holding groove via the elastic element.

5. The measuring chamber as claimed in claim 1, wherein a first blind hole is formed in a center of a bottom surface of a cover plate of the upper cover; a center of a bottom surface of the first blind hole is protruded sequentially and downward to form a first cylinder and a second cylinder; a diameter of the first cylinder is greater than that of the second cylinder; a limit step is formed at a junction of the first cylinder and the second cylinder; a step hole is formed in a center of the second surface of the top plate of the reaction cup turntable; the step hole comprises a big hole and a small hole; the big hole is located above the small hole; a step surface is formed at a junction of the big hole and the small hole; a bearing is provided in the big hole; the second cylinder is provided in the bearing in a sleeving manner; and the bearing is limited between the limit step and the step surface along an axial direction.

6. The measuring chamber as claimed in claim 5, wherein the second surface of the top plate of the reaction cup turntable is shaped convexly at a periphery of the big hole to form a second annular truncated cone; and the second annular truncated cone is provided in the first blind hole in a sleeving manner.

7. The measuring chamber as claimed in claim 2, wherein a first labyrinth structure is formed at a junction of the top of the outer shell and the reaction cup turntable; the first labyrinth structure comprises a first annular lug boss and a first annular groove; the outer shell is formed into either of the first annular lug boss and the first annular groove; and the reaction cup turntable is formed into the other of the first annular lug boss and the first annular groove.

8. The measuring chamber as claimed in claim 7, wherein the outer shell is of a cylindrical shape; the top plate of the reaction cup turntable is shaped convexly and outward along a radial direction to form the first annular log boss; an inner cavity of the outer shell is a step hole; the step hole of the outer shell comprises a first hole and a second hole; the first annular groove is formed at a junction of the first hole and the second hole; and the first annular lug boss is embedded into the first annular groove and can be slid relative to the first annular groove.

9. The measuring chamber as claimed in claim 2, wherein a second labyrinth structure is formed at a junction of the top of the inner shell and the reaction cup turntable; the second labyrinth structure comprises a second annular lug boss and a second annular groove; the reaction cup turntable is formed into either of the second annular lug boss and the second annular groove; and the top of the inner shell is formed into the other of the second annular lug boss and the second annular groove.

10. The measuring chamber as claimed in claim 9, wherein the peripheral wall is formed by extending an outer edge of the top plate vertically; the peripheral wall surrounds the central axial line of the reaction cup turntable so as to form the inner cavity of the reaction cup turntable; the inner shell is located in the inner cavity of the reaction cup turntable; the inner shell is located between the first surface of the top plate of the reaction cup turntable and the bottom plate along an axial direction; the second annular lug boss is located at one end, close to the reaction cup turntable, of the inner shell; the first surface of the top plate of the reaction cup turntable is protruded to form a first annular truncated cone; the second annular groove is formed along a periphery of the first annular truncated cone; and the second annular lug boss is embedded into the second annular groove and can be slid relative to the second annular groove.

11. The measuring chamber as claimed in claim 2, wherein the upper cover is fixed on the outer shell; a third labyrinth structure is formed at a junction of the top of the outer shell and the upper cover; the third labyrinth structure comprises a third annular lug boss and a third annular groove; the upper cover is formed into either of the third annular lug boss and the third annular groove; and the outer shell is formed into the other of the third annular lug boss and the third annular groove.

12. The measuring chamber as claimed in claim 11, wherein the outer shell is of a cylindrical shape; the upper cover comprises a circular cover plate and the third annular lug boss; an outer edge of the cover plate is shaped convexly to form the third annular lug boss; the third annular groove is located at one end, close to the upper cover, of the outer shell; and the third annular lug boss is matched with and abutted against the third annular groove.

13. The measuring chamber as claimed in claim 2, wherein the outer shell is of a cylindrical shape; a fourth labyrinth structure is formed at a junction of the bottom plate and the outer shell; the fourth labyrinth structure comprises a fourth annular lug boss and a fourth annular groove; the bottom plate is formed into either of the fourth annular lug boss and the fourth annular groove; the outer shell is formed into the other of the fourth annular lug boss and the fourth annular groove; an outer edge of the bottom plate is shaped convexly to form the fourth annular lug boss; the fourth annular groove is located at one end, close to the bottom plate, of the outer shell; and the fourth annular lug boss is matched with and abutted against the fourth annular groove.

14. The measuring chamber as claimed in claim 13, wherein a fifth labyrinth structure is formed at a junction of the bottom plate and the reaction cup turntable; the fifth labyrinth structure comprises a fifth annular lug boss and a fifth annular groove; the bottom plate is formed into either of the fifth annular lug boss and the fifth annular groove; the reaction cup turntable is formed into the other of the fifth annular lug boss and the fifth annular groove; the fifth annular lug boss is located on the bottom plate; the outer edge of the bottom plate is shaped convexly to form the fourth annular lug boss; an inner diameter of the fifth annular lug boss is smaller than that of the fourth annular lug boss; central axial lines of the fifth annular lug boss and the fourth annular lug boss are the same; the fifth annular groove is located at one end, close to the bottom plate, of the reaction cup turntable; and the fifth annular lug boss is embedded into the fifth annular groove and can be slid relative to the fifth annular groove.

15. The measuring chamber as claimed in claim 2, further comprising a driving mechanism, wherein the outer shell, the inner she and the bottom plate are fixed and integrated together; a first through hole is formed on the bottom plate; the inner shell surrounds the first through hole; the outer shed surrounds the inner shell; the outer shell and the inner shell are arranged at intervals; and the driving mechanism is connected with the reaction cup turntable via the first through hole, so as to drive the reaction cup turntable to rotate.

16. The measuring chamber as claimed in claim 15, wherein the upper cover is fixed on the outer shell; a first labyrinth structure is formed at a junction of the top of the outer shell and the reaction cup turntable; and/or a second labyrinth structure is formed at a junction of a top of the inner shell and the reaction cup turntable.

17. The measuring chamber as claimed in claim 2, further comprising a driving mechanism, wherein a first through hole is formed on the bottom plate; the bottom plate is formed into a fourth annular lug boss and a fifth annular lug boss inward and sequentially along a radial direction of the first through hole; the fourth annular lug boss is formed at an outer edge of the bottom plate and shaped convexly and upward; central axial lines of the fifth annular lug boss, the fourth annular lug boss and the first through hole are the same; an inner diameter of the fifth annular lug boss is smaller than that of the fourth annular lug boss; a first holding groove is formed between the fourth annular lug boss and the fifth annular lug boss; a second holding groove is formed between the fifth annular lug boss and the first through hole; the outer shell and a bottom of the reaction cup turntable are located in the first holding groove; a bottom of the inner shell is located in the second holding groove; and the driving mechanism is connected with the reaction cup turntable by passing through the first through hole, so as to drive the reaction cup turntable to rotate.

18. The measuring chamber as claimed in claim 2, wherein the outer shell and the inner shell are fixed on the bottom plate; the upper cover is fixed on the outer shell; a first labyrinth structure is formed at a junction of the outer shell and the reaction cup turntable; a second labyrinth structure is formed at a junction of the inner shell and the reaction cup turntable; a third labyrinth structure is formed at a junction of the outer shell and the upper cover; a fourth labyrinth structure is formed at a junction of the outer shell and the bottom plate; and a fifth labyrinth structure is formed at a junction of the bottom plate and the reaction cup turntable.

19. The measuring chamber as claimed in claim 1, wherein the plurality of reaction cup processing stations comprises:
- a first reaction cup processing station, a reaction cup being placed into or taken out of the measuring chamber at the first reaction cup processing station;
- a second reaction cup processing station, the first substrate nozzle being provided at the second reaction cup processing station so as to add an excitation substrate I to the reaction cup;
- a third reaction cup processing station, the photomultiplier detection component being provided at the third reaction cup processing station; and
- a fourth reaction cup processing station, the waste liquor adsorption needle component being provided at the fourth reaction cup processing station so as to extract waste liquor of the reaction cup;
- wherein the third reaction cup processing station and the adjacent second reaction cup processing station and fourth reaction cup processing station are sealed in a mutually light-isolated manner.

* * * * *